United States Patent [19]
Molter et al.

[11] Patent Number: 5,651,929
[45] Date of Patent: Jul. 29, 1997

[54] HIGH PERFORMANCE ELECTROLYTIC CELL ELECTRODE STRUCTURES AND A PROCESS FOR PREPARING SUCH ELECTRODE STRUCTURES

[75] Inventors: Trent M. Molter; Kurt M. Critz, both of Enfield, Conn.

[73] Assignee: United Technologies Corporation, Hartford, Conn.

[21] Appl. No.: 513,081

[22] Filed: Aug. 9, 1995

Related U.S. Application Data

[62] Division of Ser. No. 188,487, Jan. 28, 1994, Pat. No. 5,470,448.

[51] Int. Cl.[6] .................. C04B 35/00; H01M 4/88; C25B 13/04
[52] U.S. Cl. .................. 264/104; 429/40; 204/282; 204/296
[58] Field of Search .................. 429/40, 41, 42, 429/43; 204/282, 283, 296; 521/27; 264/104

[56] References Cited

U.S. PATENT DOCUMENTS 5,266,177  11/1993  Watanabe et al. ................. 429/40

FOREIGN PATENT DOCUMENTS

0631337A2  6/1994  European Pat. Off. .
2549083    5/1977  Germany .
54-110435  8/1979  Japan .

OTHER PUBLICATIONS

Abstract of DE 2549083 (H. Meier) May 5, 1977.
Abstract of JP 54110435 (Hiroshi et al.) Aug. 29, 1979.
Bibliographic data for JP 54110435 (Hiroshi et al.) Aug. 29, 1979.

*Primary Examiner*—Kathryn L. Gorgos
*Assistant Examiner*—Alex Noguerola
*Attorney, Agent, or Firm*—Mary R. Bonzagni, Esq.; Holland & Bonzagni, P.c.

[57] ABSTRACT

A high performance ionomer assisted electrolytic cell electrode structure is provided. Such structures operate effectively at catalyst loadings as low as 0.10 mg/cm$^2$ and demonstrate increased structural integrity without ionomer degradation. The inventive structure comprises a hydrated ion exchange membrane having a first surface and a second surface and at least one catalyst ionomer layer bonded to the first and/or second surface of the membrane that comprises hydrated and swollen ionomer solids bonded to discrete catalyst particles.

5 Claims, 2 Drawing Sheets

HIGH PERFORMANCE ELECTROLYTIC CELL ELECTRODE STRUCTURES AND A PROCESS FOR PREPARING SUCH ELECTRODE STRUCTURES

This is a division of application Ser. No. 08/188,487, field on Jan. 28, 1994, now U.S. Pat. No. 5,470,448.

BACKGROUND OF THE INVENTION

1. Field of the Invention

This invention relates generally to high performance ionomer assisted electrolytic cell electrode structures; a process for preparing such electrode structures; and to an electrolysis cell employing such high performance electrode structures.

2. Description of Related Art

Electrolysis cells and fuel cells are basically energy conversion devices and include liquid electrolyte cells and solid or membrane electrolyte cells. Electrolysis and fuel cells are structurally similar, but are utilized to effect different half-cell reactions. Therefore, each type of cell relies upon different conditions for the maintenance of high ion conductivity within the cell. In particular, electrolysis cells require the movement of appropriate quantities of water to the catalyst sites and the simultaneous movement of gas away from the catalyst sites. Additionally, it is necessary to maintain high ion conductivity within the cell. Fuel cells, in contrast, require that water be repelled from the electrode in order to prevent flooding. Water is continuously drained out of these cells during operation. It is also necessary in fuel cells to provide a high flux of ions to and from the active electrode sites.

Membrane electrolysis cells and membrane fuel cells typically comprise an anode, a cathode, an ion exchange membrane disposed therebetween, for providing ion exchange between the cathode and the anode electrodes, an anode chamber and a cathode chamber. Such cells offer many advantages, including the ability of ion exchange membranes to resist depletion or degradation, the ability to provide positive separation of process fluids and the membranes easy incorporation into electrolysis cell and fuel cell structures. However, as alluded to above, the half-cell reactions that take place at the anode and cathode require catalysts to proceed at useful rates. Accordingly, techniques have been developed to incorporate catalyst materials into membrane electrolysis cells and fuel cells.

Catalyst materials were first incorporated into such cells by hot pressing the materials directly into the surface of the membrane. High catalyst loadings were necessary, however, to achieve useful current densities.

Efforts directed toward reducing catalyst loadings in fuel cells include the use of carbon-based electrode structures that comprise platinum loaded carbon particles on a carbon cloth or carbon paper electrode substrate, bound together by a hydrophobic component such as polytetrafluoroethylene (PTFE) or Teflon®. Such a structure is disclosed in U.S. Pat. No. 4,876,115, issued Oct. 24, 1989. In addition to hydrophobicity, Teflon® is taught as providing gas access with the electrode. (See Col. 4, lines 22 to 26.) The catalyzed sides of the carbon electrodes of the '115 patent are impregnated to a depth of about 10 micrometers (μ) with a solubilized form of ionomer to increase the access of the electrolyte to the catalyst within the catalyst-C/Teflon® layer. Application of such ionomer materials is by spraying or by deposit with an applicator onto the surface of the electrode. (See Col. 4, lines 66 to 68.) However, due to varying thicknesses in the catalyst layer, uneven impregnation of the solubilized ionomer in the catalyst layer results. It has been observed that some areas of the impregnated electrode are not fully impregnated while other areas have ionomer material extending so far within the electrode that gas diffusion through the electrode is impeded. It has been further observed that hydrophobic binders, such as Teflon® block proton and oxygen access to catalyst sites and that differential swelling between the ionomer material and catalyst layer result in delamination with resulting discontinuity in the ion path and decreased cell longevity.

An attempt to overcome these deficiencies is described in U.S. Pat. No. 5,234,777, issued Aug. 10, 1993. The '777 patent is directed to an improved solid polymer electrolyte membrane assembly where the improvement comprises a membrane and a film of a proton conducting material or binder having a supported platinum catalyst uniformly dispersed therein, where the film is bonded to the membrane. The catalyst/binder layer can be fabricated as a separate unit and transferred to the surface of the membrane by hot pressing at temperatures between 125° C. and 145° C. onto the membrane (see Col. 5, lines 3 to 7) or can be directly applied, in the form of an ink, to the surface of the membrane at temperatures of at least 150° C. (see Col. 6, lines 27 to 36). This high temperature application and subsequent drying reportedly cures the catalyst layer.

It has been observed however that painting and baking such liquid coatings or inks results in cracking and shrinkage and therefore voids resulting in discontinuity. In addition, applying the ink directly to the surface of the membrane results in varying thicknesses of the resulting film and small voids due to ink movement during application and nonuniform membrane thicknesses. Moreover, such films degrade and are rendered less hydrophilic when heated to elevated temperatures and, as a result, reduced ion conductivity is observed in electrolysis cells employing such membrane assemblies. Further, it is theorized that the bonding between the catalyst and the ionomer material is weak, where moderate catalyst/ionomer dispersion formation temperatures are employed, thereby resulting in decreased activity at the catalyst/ionomer interfaces. Finally, it is theorized that the absence of a rehydration step in the method for preparing such a membrane assembly further results in a decrease in observed ion conductivity.

Accordingly, it is an object of the present invention to provide ionomer assisted electrode structures that enhance electrolysis cell performance; that demonstrate increased structural integrity; and that have low catalyst loadings.

It is another object of the present invention to provide electrode structures having catalyst ionomer layers where hydrated and swollen ionomer solids are bonded to discrete catalyst particles.

It is yet another object of the present invention to provide electrode structures having a catalyst ionomer layer located adjacent to a hydrated ion exchange membrane that demonstrate improved bonding between the catalyst ionomer layers and the membranes.

It is a further object of the present invention to provide a process for preparing such electrode structures.

It is yet a further object of the present invention to provide an electrolysis cell that employs such electrode structures.

SUMMARY OF THE INVENTION

The present invention therefore provides an improved ionomer assisted electrode structure for use in an electrolysis cell comprising an ion exchange membrane having a first surface and a catalyst ionomer layer bonded to the first surface of the ion exchange membrane, where the improvement comprises a hydrated ion exchange membrane having a first surface and a second surface and at least one catalyst ionomer layer comprising hydrated and swollen ionomer solids bonded to discrete unsupported catalyst particles, where the catalyst loading in the catalyst ionomer layer is at least 0.10 milligrams (mg)/square centimeter ($cm^2$), and where the catalyst ionomer layer is bonded to at least the first surface of the hydrated ion exchange membrane.

The present invention further provides a process for preparing an ionomer assisted electrode structure as described hereinabove, comprising the steps of:

1. forming an aqueous solution comprising from about 0.10 to about 20% by weight swollen ionomer solids and from about 0.15 to about 30% by weight catalyst;

2. heating the solution to a temperature from about 40° C. to about 110° C. until a dry powder residue remains;

3. forming a solid paste comprising a quantity of the dry powder residue and a quantity of a fast drying or subliming agent;

4. pressing the solid paste onto at least the first surface of an ion exchange membrane at a temperature from about 121° C. to about 232° C. and at a pressure of from about 2.1 to about 27.6 megapascals (MPa); and 5. rehydrating the ion exchange membrane and the ionomer solids of the solid paste.

The present invention also provides an electrolysis cell utilizing at least one ionomer assisted electrode structure as described above.

DETAILED DESCRIPTION OF THE INVENTION

Figure 1:
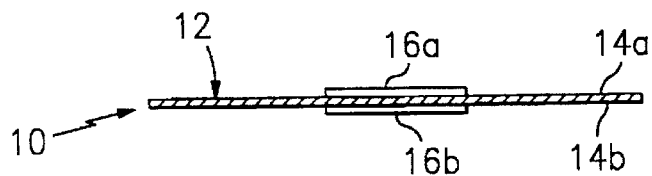
FIG. 1 is a cross section of a preferred electrode structure of the present invention.

The ion exchange membrane of the present invention can be any membrane of a hydrophilic ion exchange resin capable of effectively transporting protons and water. Useful membranes include perfluorinated membranes such as perfluorocarboxylic acid membranes and perfluorosulfonic acid membranes. The preferred ion exchange membranes are sold by E.I. Dupont De Nemours, Inc., Wilmington, Del., under the product designation Nafion® perfluorosulfonic acid membranes.

Where such membranes are typically relieved of some water during fabrication of the inventive electrode structure it is preferred that such membranes be rehydrated prior to operation of the host electrolysis cell. It has been demonstrated that non-fully hydrated membranes display decreased water transport capabilities which results in lower water activity at the electrode surface. It has been further demonstrated that rehydration of the ion exchange membrane will not occur during a typical water electrolysis reaction.

The catalyst ionomer layer of the present invention comprises hydrated and swollen ionomer solids and discrete catalyst particles. It is preferred that the catalyst ionomer layer have a catalyst loading of at least 0.10 $mg/cm^2$ and more preferably have a catalyst loading of between about 0.5 $mg/cm^2$ to about 6.0 $mg/cm^2$.

The ionomer solids of the catalyst ionomer layer can be any swollen proton and water conducting material. The term "swollen" as used herein is intended to mean a partially disassociated polymeric material. It is theorized that under appropriate fabrication or processing conditions the swollen ionomer solids bond to the catalyst particles, thereby resulting in increased structural integrity and increased catalytic activity at the ionomer/catalyst interfaces. Suitable ionomers include those having a hydrocarbon backbone and perfluoroionomers such as perfluorosulfonate ionomers, which have a fluorocarbon backbone. The preferred ionomers are perfluorosulfonate ionomers available from Dow Chemical Co., Midland, Mich., or perfluorosulfonate ionomers available from E.I. DuPont De Nemours, Inc., under the product designation Nafion® perfluorosulfonate ionomers.

These materials are similarly relieved of water during fabrication of the present inventive electrode structure and therefore it is preferred that these materials be hydrated as well before operation of the host electrolysis cell.

The catalyst of the present invention includes supported and unsupported metal, metal oxide and organometallic catalysts. Unsupported catalysts are preferred where they tend to disperse more readily in aqueous media. Particular catalysts useful in the present invention include metal catalysts such as platinum, ruthenium, iridium, osmium, gold, rhodium, palladium, tin, indium, tungsten, nickel and their oxides. Additional useful catalysts include graphite and organometallics, such as pthalocyanines and porphyrins. The preferred catalyst is unsupported platinum (Pt) catalyst or unsupported platinum group catalyst admixes or alloys.

Referring to FIG. 1, reference numeral 10 generally designates a preferred ionomer assisted electrode structure of the present invention. Electrode structure 10 generally includes a hydrated ion exchange membrane 12 having a first surface 14a and a second surface 14b and two catalyst ionomer layers 16a, 16b where catalyst ionomer layer 16a is bonded to the first surface 14a of ion exchange membrane 12 and where catalyst ionomer layer 16b is bonded to the second surface 14b of ion exchange membrane 12.

In a preferred process for preparing the present inventive electrode structure 10 an aqueous solution is formed which contains from about 0.10 to about 20% by weight and preferably from about 0.10 to about 2.0% by weight swollen ionomer solids and from about 0.15 to about 30% by weight and preferably from about 0.65 to about 13% by weight catalyst. The aqueous solution is heated to a temperature from about 40° C. to about 110° C. and preferably to a temperature from about 95° C. to about 105° C. until a dry powder residue remains. A quantity of the dry powder residue is then mixed with a quantity of a fast drying or subliming agent, such as dry ice, so as to form a solid paste. The solid paste is then preferably spread out onto any appropriate releasable surface to a thickness of from about 0.32 to about 0.64 centimeters (cm) and preferably to a thickness of from about 0.42 to about 0.53 cm and allowed to dry or sublimate to form the catalyst ionomer layer 16a. For ease of reference the term ion exchange membrane 12 as used hereinbelow will refer to both hydrated membranes and partially dehydrated membranes. In addition, the term catalyst ionomer layer 16a, 16b will refer to both hydrated and partially dehydrated layers. The catalyst ionomer layer 16a is then pressed onto the first surface 14a of the ion exchange membrane 12 at a temperature of from about 121° C. to about 232° C., preferably from about 163° C. to about 182° C., and at a pressure from about 2.1 to about 27.6 MPa, preferably from about 6.9 to about 20.7 MPa. The catalyst ionomer layer 16b is then similarly prepared and pressed onto the second surface 14b of the ion exchange membrane 12 and the ion exchange membrane 12 and ionomer solids of the catalyst ionomer layers 16a, 16b rehydrated to form the preferred electrode structure 10 of the present invention. Rehydration of the ion exchange membrane 12 and ionomer solids preferably involves heating the electrode structure 10 in deionized water to a temperature of from about 90° C. to about 110° C. for from about 15 minutes to about 3 hours and more preferably from about 45 minutes to about 1 hour and 15 minutes.

In preparing the swollen ionomer solids for use in the present invention, it is preferred that the process disclosed in U.S. Pat. No. 4,433,082 to Grot, which is incorporated herein by reference, be employed. In particular, it is preferred that dry, sheet form, ionomer membrane material, in the proton form, be cut or ground into pieces measuring 0.16 cm ×0.16 cm×0.16 cm or smaller. The resulting material is then preferably placed in a pressure bomb along with a water/alcohol (i.e. isopropanol) mixture containing from about 40% to about 60% by volume water and from about 40% to about 60% by volume alcohol. The pressure bomb is then sealed and brought to a temperature of from about 275° C. to about 300° C. which generally produces a vapor pressure of from about 6.9 to about 13.8 MPa. It is further preferred that the mixture inside the pressure bomb remain at pressure for about 30 minutes to about 2 hours. The mixture is then removed from the pressure bomb and the light byproducts, which contain swollen ionomer solids, water, residual alcohol and organics, decanted into an appropriate container and diluted with water to about a 10:1 to about a 20:1 dilution volume. The diluted mixture is then placed on a hot plate and heated to a temperature from about 80° C. to about 110° C. until the mixture volume is reduced to approximately 10% of the original dilution volume. During this preparation step it is theorized that light hydrocarbons, alcohol and a portion of the water present are driven off. The resulting reduced volume aqueous solution containing swollen ionomer solids is then analyzed to determine the total ionomer solids content. The solution volume is then adjusted, if necessary, so that its solids content falls within the preferred range of 0.10 to 20% by weight for the swollen ionomer solids as set forth above.

In forming the solid paste used to prepare the catalyst ionomer layers 16a, 16b of the present inventive electrode structure 10 it is preferred that the dry powder residue be passed through a 100 to 400 mesh screen before combining the residue with a quantity of a fast drying or subliming agent, such as dry ice. It is believed that larger mesh size particles could cause the ion exchange membrane 12 to become punctured during the subsequent pressing step.

Figure 2:
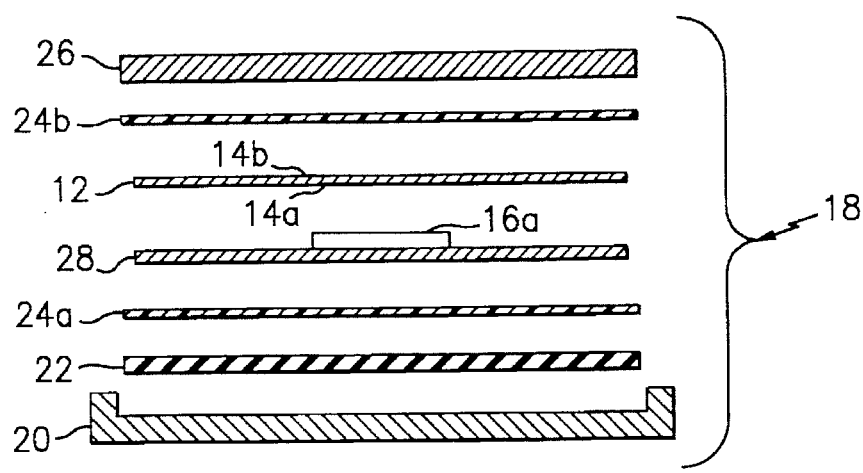
FIG. 2 is a cross section of a pressing mold used in the preparation of the present invention showing a membrane and a non-adhered catalyst ionomer layer.
Figure 3:
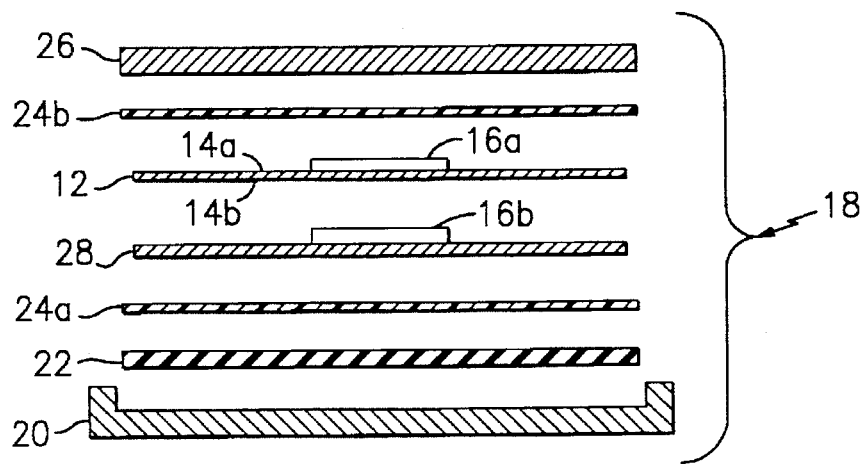
FIG. 3 is a cross section of a pressing mold showing a membrane with an adhered catalyst ionomer layer and a non-adhered catalyst ionomer layer.

In preferred solid paste formation and pressing steps, 0.1 mg to about 25 grams (g) and preferably from about 500 to about 1000 mg of dry powder residue having an average particle size of less than about 400 microns and from about 50 to about 400 milliliters (ml) and preferably from about 100 to about 200 ml of dry ice are mixed using a mortar and pestle. The residue/dry ice mixture is then quickly transferred to a titanium metal foil used in conjunction with a spreading frame, and more preferably is transferred to a titanium metal foil used in conjunction with a Lexan® spreading frame having inner dimensions equivalent to the active area of the cell and a height of less than one-half centimeter, until the mixture is flush with the top of the frame. The mixture is then allowed to dry or sublimate to form catalyst ionomer layer 16a and any visible lumps in the catalyst ionomer layer 16a removed. The spreading frame is removed and a pressing mold is then set up. Although not intended in any way to limit the present invention, FIGS. 2 and 3, and in particular, reference numeral 18 generally designates a preferred pressing mold for use in the present invention. Pressing mold 18 generally includes a bottom mold 20, a rubber layer 22, two teflon sheets 24a, 24b and a top mold 26. Such devices are well known in the art. Referring in particular to FIG. 2, reference numeral 28 generally designates the metal foil used in conjunction with the spreading frame as described above. The foil 28, with the dried or sublimed catalyst ionomer layer 16a located thereon, and the ion exchange membrane 12 having a first surface 14a and a second surface 14b are placed in the pressing mold 18. The mold 18 is then brought to a temperature of from about 121° C. to about 232° C. (preferably from about 163° C. to about 182° C.) and pressurized to from about 2.1 to about 27.6 MPa (preferably from about 6.9 to about 20.7 MPa) for from about 1 to about 10 minutes (preferably from about 5 to about 6 minutes). The temperature is then reduced and the pressure released and the membrane 12 with bonded catalyst ionomer layer 16a is removed and placed in deionized water. A catalyst ionomer layer 16b is then prepared according to the procedure detailed above. Referring to FIG. 3, metal foil 28, with the dried or sublimed catalyst ionomer layer 16b located thereon and the ion exchange membrane 12 with bonded catalyst ionomer layer 16a are placed in the pressing mold 18. As is evident from FIG. 3 the unbonded second surface 14b of the ion exchange membrane 12 is positioned so as to face the catalyst ionomer layer 16b. The pressing mold 18 is then heated and pressurized as described hereinabove. The resulting structure is then removed from the pressing mold 18 and rehydrated to form the preferred electrode structure 10 of the present invention.

Due to the tendency of ionomer materials to pick up cationic impurities, such as aluminum, copper, iron, chromium, nickel, sodium and potassium, during processing it is preferred that the electrode structure 10 be further subjected to acid rinsing before the final rehydration process step. In particular, it is preferred that the electrode structure 10 be submerged, at least once, in a 0.5 normal (N) to about 1.5N sulfuric acid solution for from about 5 minutes to about 60 minutes; be rinsed with deionized water until the pH is neutral; and then be placed in deionized water and heated to a temperature of from about 90° C. to about 110° C. for from about 15 minutes to about 3 hours and preferably from about 45 minutes to about 1 hour 15 minutes.

In addition to the above description, the high performance ionomer assisted electrolytic cell electrode of the present invention is further developed by reference to the illustrative, but not limiting, examples set forth below. In particular, by way of the following working examples the present inventive electrode structure is tested and compared to an electrode assembly prepared according to the teachings of U.S. Pat. No. 5,234,777.

WORKING EXAMPLES

In the Working Examples set forth below, the following components were used:

SOLUBILIZED IONOMER—a 5% by weight solution of perfluorosulfonate polymer in water prepared in accordance with the teachings of U.S. Pat. No. 4,433,082.

CATALYST—a mixture comprising 50.0% by weight iridium metal and mixed iridium oxides and 50.0% by weight platinum metal and mixed platinum oxides.

MEMBRANE—a perfluoroionomer membrane sold by E.I. Dupont De Nemours Inc. under the name Nafion® 117 perfluoroionomer membrane.

SAMPLE PREPARATION

Two types of electrode structures were fabricated in an effort to compare and contrast the performance and integrity of the present inventive electrode structure and an electrode assembly prepared according to the teachings of U.S. Pat. No. 5,234,777. Electrode Structure "A", as used hereinbelow, is intended to designate the high performance ionomer assisted electrolytic cell electrode structure of the present invention. Electrode Structure "B", as used hereinbelow, is intended to designate an electrode assembly prepared according to the method set forth as "PROTOCOL I" in U.S. Pat. No. 5,234,777 at Columns 4 to 5, lines 52 to 13. It is noted that, in preparing Electrode Structure "B", an unsupported catalyst was used.

Electrode Structure "A" Preparation 5 g of MEMBRANE in the dry sheet, proton form was cut into pieces measuring 0.16 cm×0.16 cm×0.16 cm or smaller and then placed in an 1850 ml pressure bomb along with 400 ml of a 50% volumetric water-isopropanol mixture. The bomb was then sealed and brought to a temperature of 300° C. Once this temperature was reached the pressure bomb was removed from the heat. The pressure bomb was then cooled for approximately two hours, the seal broken, and 100 ml of light byproducts, which contained swollen ionomer solids, were decanted into a beaker. The decanted mixture was then diluted with water to a 100:1 dilution volume and then boiled until the volume was approximately 10% of the original dilution volume. The total swollen ionomer solids content of the reduced volume mixture was then determined as being 18.5%. This determination was achieved by boiling a 1 ml sample of the reduced volume mixture until only solids remained, weighing the solids and then determining the solids content per unit volume of the mixture. Based upon this determination, the mixture was diluted thereby achieving a mixture with an approximately 15% swollen ionomer solids content. 5 g of this diluted mixture along with 4.25 g of CATALYST and 200 ml of water were then placed in a beaker and the resulting solution boiled until only 10 to 20 ml of solution remained in the beaker. The remaining solution was then washed into a dish which was then placed into an oven maintained at approximately 75° C. The solution remained in the oven for 16 hours resulting in a dry powder residue. The residue was then passed through a 400 mesh screen, milled with 150 to 200 ml of dry ice using a mortar and pestle and spread out onto a piece of metal foil used in conjunction with a spreading frame to form a circular decal measuring approximately 0.05 ft$^2$ and having a catalyst loading of approximately 2 mg/cm$^2$. The decal was allowed to dry and the metal foil containing the dried decal was then placed in a pressing mold containing a MEMBRANE measuring 12.7 cm×12.7 cm, as best shown in FIG. 2. The mold was then brought to a temperature of 177° C., pressurized to 13.1 MPa, and these conditions maintained for 6 to 8 minutes. The mold temperature was then reduced and the pressure released. The resulting electrode structure was then placed in deionized water. Subsequently, the electrode structure was soaked in a 0.1N sulfuric acid solution for one hour, rinsed with deionized water and then boiled in deionized water for 1 hour.

Electrode Structure "B" Preparation 0.085 g of CATALYST, 0.3 g of SOLUBILIZED IONOMER, 0.5 g of water and 2.0 g of glycerol were placed in a 5 cubic centimeter (cm$^3$) glass vial. The resulting solution was sonicated for approximately 30 minutes in a water bath and then painted onto a teflon sheet to a thickness of approximately 0.003 cm. (The teflon sheet employed had been sprayed with Frekote® fluorocarbon mold release agent, available from Dexter Corporation, 1 Dexter Drive, Seabrook, N.H., prior to painting the surface with the sonicated solution.) The painted teflon sheet was then dried for a period of one hour in an oven maintained at 135° C. The above-referenced painting and drying steps were then repeated seven times to achieve a circular decal measuring approximately 0.05 ft$^2$ and having a catalyst loading of approximately 2 mg/cm$^2$. The resulting electrode assembly was then pressed to a MEMBRANE measuring 12.7 cm×12.7 cm using the pressing mold setup used in the Electrode Structure "A" Preparation Method at 125° C. and at a pressure of 90 atmospheres (atm) for 90 seconds. The mold temperature was then reduced, the pressure relieved and the cooled electrode assembly removed.

TEST METHODS

Electrode Structures "A" and "B" were then subjected to the following examination/tests:

Visual Examination—Electrode Structures "A" and "B" were visually examined in an effort to identify voids, discontinuities and delaminations.

Electrode Adhesion Test—Electrode Structures "A" and "B" were each placed in separate one liter beakers containing distilled deionized water and sonicated for four minutes. Each electrode structure was then removed and the water in each beaker evaporated leaving behind residual catalyst particles which had been dislodged from each electrode assembly or structure. The percentage of catalyst lost from each electrode structure was then determined by dividing the mass of the catalyst dislodged from the electrode structure by the original mass of the catalyst applied. This quantity was then multiplied by 100.

Electrode Performance Test—A low pressure electrolyzer for electrolyzing water to hydrogen and oxygen gas was employed to compare Electrode Structures "A" and "B" in terms of "inherent current density capability" and "voltage/power requirements at equivalent current densities". The low pressure electrolyzer basically comprised an anode chamber ($O_2$ compartment), a cathode chamber ($H_2$ compartment), a cathode electrode (fuel cell grade platinum black, obtained from Engelhard Corp., 554 Engelhard Drive, Seneca, S.C., blended with 15% Teflon), and either Electrode Structure "A" or Electrode Structure "B". The operating parameters for each test conducted using the low pressure electrolyzer with either Electrode Structure "A" or "B" mounted therein were as follows:

| | |
|---|---|
| temperature (°C.) | 36 |
| water flow rate (ml/minute) | 70 |
| pressure | |
| ($H_2$ compartment) (MPa) | 0.1 |
| ($O_2$ compartment) (MPa) | 0.1 |
| current density increments (amperes (amps)/ft$^2$) | 25 |

For each test, water was introduced into the cathode chamber of the electrolyzer. The current density within the electrolyzer was ramped in discrete increments of 25 amps/ft$^2$ to 50 amps/ft$^2$, the resultant electrolyzer voltage monitored for a period of five minutes in order to establish equilibrium and then recorded. The current density was then incrementally increased by factors of 25 and equilibrated resultant voltages recorded. For each test the current density was incrementally increased until the "limiting current density" for the subject electrode structure was reached. The term "limiting current density", as used herein, is intended to mean the maximum current density at which the electrolyzer can operate with a "stable resultant voltage". "Stable resultant voltage", as used herein, is intended to mean voltages that do not change for a period of at least five minutes.

EXAMPLES C1 TO C2 AND 1 TO 2

In these Examples, electrode structures prepared as set forth above were examined for voids, discontinuities and delaminations and then tested for electrode or catalyst ionomer layer adhesion, integrity and durability. The results are displayed in Table I.

TABLE I

SUMMARY OF EXAMPLES C1 TO C2 AND 1 TO 2

| EXAMPLE Electrode Structure | 1 "A" | C1 "B" | 2 "A" | C2 "B" |
|---|---|---|---|---|
| PROPERTIES | | | | |
| surface uniformity and ease of delamination[1] | uniform, adherent | somewhat non-uniform in that several large voids existed in the structure electrode or composite film readily delaminated from the membrane | | |
| Electrode structural integrity[2] (% by weight of catalyst lost during sonication step) | | | 4.9 | 54.9 |

[1]As determined by visual examination of the subject electrode structures.
[2]As determined by the Electrode Adhesion Test described hereinabove.

Example 1 demonstrates that the electrode structure of the present invention offers surface uniformity and improved adherence of the catalyst ionomer layer or electrode to the membrane. Moreover, Example 2 demonstrates noteworthy improvement in the adhesion, integrity and durability of the catalyst ionomer layer or electrode of the present inventive electrode structure. In contrast, comparative Example C1 displayed a somewhat nonuniform surface and a composite film or electrode that was readily delaminated from its membrane. More importantly, comparative Example C2 lost over 50% of the catalyst from its composite film during sonication, thereby demonstrating decreased adhesion between the catalyst and the ionomer of its composite film.

EXAMPLES C3 AND 3

In the following Examples, the performance of a low pressure electrolyzer having either Electrode Structure "A" or "B" mounted therein, was evaluated in terms of inherent current density capability and voltage/power requirements at incrementally increased current densities. The results are set forth in tabular format in Table II and are set forth in plotted format in FIG. 4.

TABLE II

SUMMARY OF EXAMPLES C3 AND 3

| EXAMPLE Electrode Structure | Electrolyzer Voltage[1] (Volts) | |
|---|---|---|
| Current Density (amps/ft$^2$) | 3 "A" | C3 "B" |
| 50 | 1.924 | 2.09 |
| 75 | 1.977 | 2.31 |
| 100 | 2.031 | 2.607 |
| 125 | 2.082 | 2.935 |
| 150 | 2.114 | |
| 175 | 2.158 | |
| 200 | 2.181 | |
| 225 | 2.237 | |
| 250 | 2.271 | |
| 275 | 2.314 | |
| 300 | 2.441 | |

[1]As determined by the Electrode Performance Test described hereinabove.

Figure 4:
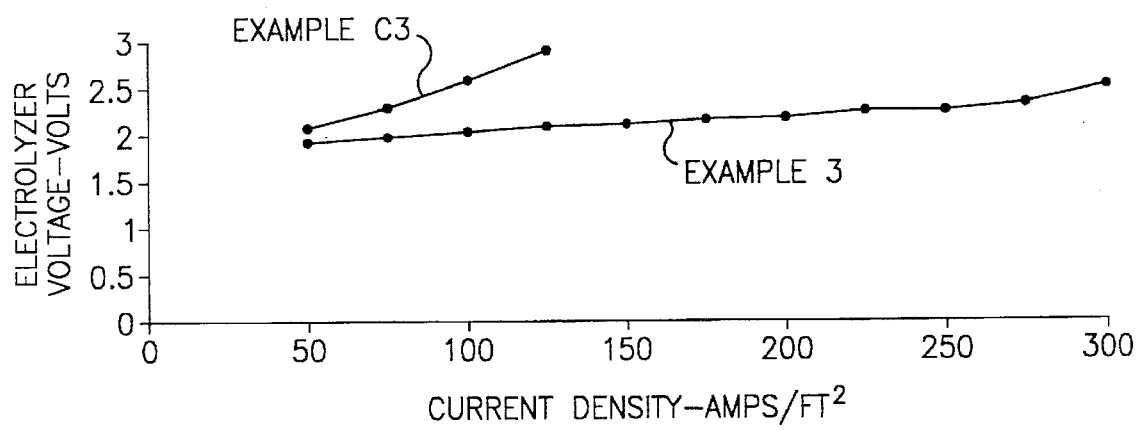
FIG. 4 is a graph of electrolyzer voltage versus current density behavior comparing a low pressure electrolyzer employing the present invention with an electrolyzer employing a prior art device.

Example 3 as set forth in both Table II and FIG. 4 clearly demonstrates that electrolyzers employing the present inventive electrode structure offer superior performance capability as compared to the electrolyzer in comparative Example C3 which employed an electrode assembly prepared according to the methodology taught in U.S. Pat. No. 5,234,777. Referring in particular to FIG. 4, Example 3, the inventive electrode structure's superior performance is shown by the overall lower electrolyzer voltage required for the generation of $H_2$ and $O_2$ at equivalent current densities for electrolyzers employing the present inventive electrode structure. The superior performance of the present inventive electrode structure is further shown by the greater limiting or inherent current density capability of electrolyzers employing the present invention.

Although this invention has been shown and described with respect to detailed embodiments thereof, it would be understood by those skilled in the art that various changes in form and detail thereof may be made without departing from the spirit and scope of the claimed invention.

Having thus described the invention, what is claimed is:

1. A process for preparing an ionomer assisted electrode structure for use in an electrolysis cell, wherein said electrode structure comprises a hydrated ion exchange membrane having a first surface and a second surface and at least one catalyst ionomer layer, wherein said catalyst ionomer layer comprises hydrated and swollen ionomer solids bonded to discrete catalyst particles, wherein said catalyst ionomer layer is bonded to at least said first surface of said hydrated ion exchange membrane, and wherein said process comprises the steps of:
   a. forming an aqueous solution comprising from about 0.10 to about 20% by weight swollen ionomer solids and from about 0.15 to about 30% by weight catalyst, based on the total weight of said aqueous solution;
   b. heating said solution to a temperature of from about 40° C. to about 110° C. until a dry powder residue remains;
   c. forming a homogeneous solid paste comprising a quantity of said dry powder residue and a quantity of a fast drying or subliming agent;
   d. pressing said homogeneous solid paste onto at least said first surface of said ion exchange membrane at a temperature of from about 121° C. to about 232° C. and at a pressure of from about 2.1 to about 27.6 MPa;

e. optionally repeating steps (a) through (d) wherein said homogeneous solid paste is pressed onto said second surface of said ion exchange membrane; and f. rehydrating said ion exchange membrane and said ionomer solids of said homogeneous solid paste.

2. The process for preparing an ionomer assisted electrode structure of claim 1 which further comprises the steps of:

a. acid rinsing said ion exchange membrane and said catalyst ionomer layer or layers of said electrode structure to remove cation impurities;

b. rinsing said acid rinsed ion exchange membrane and said catalyst ionomer layer or layers of said electrode structure with deionized water; and c. rehydrating said ion exchange membrane and said catalyst ionomer layer or layers of said electrode structure.

3. The process for preparing an ionomer assisted electrode structure of claim 1 wherein the step of forming an aqueous solution comprises the steps of:

a. mixing a quantity of ionomer solids with a mixture comprising water and alcohol to form an ionomer solids mixture;

b. forming a layered ionomer solids mixture having at least a first layer comprising swollen ionomer solids, water, residual alcohol and organics and a second layer by subjecting said mixture to temperatures of from about 275° C. to about 300° C. and to pressures of from about 6.9 to about 13.8 MPa for at least 30 minutes;

c. decanting a volume of said first layer of said layered ionomer solids mixture;

d. diluting said volume of said first layer with deionized water;

e. reducing said volume of said first layer at least by 50%; and f. optionally adjusting said volume of said first layer to obtain a first layer having a total ionomer solids content of from about 0.10 to about 20% by weight, based on the total weight of said volume of said first layer.

4. The process for preparing an ionomer assisted electrode structure of claims 1 or 2 wherein the rehydrating step comprises heating said electrode structure in deionized water to a temperature of from about 90° C. to about 110° C. for from about 15 minutes to about 3 hours.

5. The process for preparing an ionomer assisted electrode structure of claim 1 wherein the step of forming a solid paste further includes the step of: passing said dry powder residue through a screen having an average mesh size of from about 100 to about 400.

* * * * *